United States Patent
Fang et al.

(10) Patent No.: US 11,839,877 B2
(45) Date of Patent: Dec. 12, 2023

(54) PRESERVATION TUBE FOR SAMPLING SWAB

(71) Applicant: DA AN GENE CO., LTD., Guangdong (CN)

(72) Inventors: Pengyu Fang, Guangdong (CN); Xiwen Jiang, Guangdong (CN)

(73) Assignee: DA AN GENE CO., LTD., Guangdong (CN)

( * ) Notice: Subject to any disclaimer, the term of this patent is extended or adjusted under 35 U.S.C. 154(b) by 215 days.

(21) Appl. No.: 17/273,734

(22) PCT Filed: Oct. 27, 2020

(86) PCT No.: PCT/CN2020/124135
§ 371 (c)(1),
(2) Date: Mar. 5, 2021

(87) PCT Pub. No.: WO2021/227380
PCT Pub. Date: Nov. 18, 2021

(65) Prior Publication Data
US 2022/0032287 A1    Feb. 3, 2022

(30) Foreign Application Priority Data
May 11, 2020 (CN) .......................... 202010392717.0

(51) Int. Cl.
*B01L 3/00* (2006.01)
(52) U.S. Cl.
CPC .......... *B01L 3/5029* (2013.01); *B01L 2200/16* (2013.01); *B01L 2300/042* (2013.01); *B01L 2300/0832* (2013.01)
(58) Field of Classification Search
CPC ............... B01L 3/5029; B01L 2200/16; B01L 2300/042; B01L 2300/0832; A61B 10/02
See application file for complete search history.

(56) References Cited

U.S. PATENT DOCUMENTS

| | | | | | |
|---|---|---|---|---|---|
| 4,184,483 A | * | 1/1980 | Greenspan | ............... | C12Q 1/24 435/304.2 |
| 4,813,432 A | * | 3/1989 | Saint-Amand | ........ | B01L 3/5029 600/572 |

(Continued)

FOREIGN PATENT DOCUMENTS

| | | |
|---|---|---|
| CN | 201441389 | 4/2010 |
| CN | 102854034 | 1/2013 |

(Continued)

OTHER PUBLICATIONS

"International Search Report (Form PCT/ISA/210) of PCT/CN2020/124135," dated Jan. 28, 2021, pp. 1-5.

*Primary Examiner* — Matthew D Krcha
*Assistant Examiner* — Austin Q Le
(74) *Attorney, Agent, or Firm* — JCIP GLOBAL INC.

(57) ABSTRACT

The present invention relates to the technical field of sample preservation, and more specifically, to a preservation tube for a sampling swab which includes a tube body. A first cavity for storing a sample releasing agent and a second cavity for placing the sampling swab are provided in the tube body, the first cavity is in communication with the second cavity, and a central axis of the second cavity deviates from a central axis of the tube body. When the present invention is in use, the sampling swab is placed in the second cavity, moved up and down and rotated to elute in the second cavity, and nucleic acid samples of the sampling swab are evenly distributed in the sample releasing agent, and can be used for detection after sucking the sample releasing agent in the first cavity.

12 Claims, 10 Drawing Sheets

(56) References Cited

U.S. PATENT DOCUMENTS

| | | | |
|---|---|---|---|
| 2004/0184954 A1 | 9/2004 | Guo et al. | |
| 2004/0237674 A1 | 12/2004 | Wu et al. | |
| 2009/0030342 A1* | 1/2009 | Flanigan | B01L 3/5029 |
| | | | 600/572 |
| 2013/0175266 A1* | 7/2013 | Ellis | B01L 3/502 |
| | | | 220/23.87 |
| 2019/0344263 A1* | 11/2019 | Irmscher | F04B 13/00 |

FOREIGN PATENT DOCUMENTS

| | | | | |
|---|---|---|---|---|
| CN | 104921760 | | 9/2015 | |
| CN | 105748108 | | 7/2016 | |
| CN | 107036848 | | 8/2017 | |
| KR | 20130140392 A | * | 5/2015 | A61B 10/02 |

* cited by examiner

PRESERVATION TUBE FOR SAMPLING SWAB

CROSS-REFERENCE TO RELATED APPLICATION

This application is a 371 of international application of PCT application serial no. PCT/CN2020/124135, filed on Oct. 27, 2020, which claims the priority benefit of China application no. 202010392717.0, filed on May 11, 2020. The entirety of each of the above mentioned patent applications is hereby incorporated by reference herein and made a part of this specification.

TECHNICAL FIELD

The present invention relates to the technical field of sample preservation, and more specifically, to a preservation tube for a sampling swab.

BACKGROUND

In the field of in vitro diagnosis, especially genetic diagnosis, it is necessary to collect samples isolated from the human body for testing, and sampling with sampling swabs is a simple, painless, and non-invasive DNA specimen collection method. This method is suitable for collecting DNA samples from people of any age. A swab is usually used as a tool for medical examination to collect microorganisms, exfoliated cells or secretions and a sampling swab is stored in a preservation tube and sent for inspection. The current sampling swab preservation tube includes a detachable tube body and a cover body. The sampling swab is sealed in the tube body after collecting patient samples, and then is sent to a laboratory for nucleic acid extraction and testing. However, there are many shortcomings in this current way: (1) in the process of nucleic acid extraction in the laboratory, the nucleic acid sample on the swab needs to be oscillated and eluted, which is cumbersome and increases the risk of infection caused by transferring the sample; and (2) in the process of detection, since there is no structure for fixing the sampling swab in the preservation tube, and the swab is easy to tilt in the preservation tube, which affects the detection and sampling operation.

SUMMARY

An objective of the present invention is to overcome the shortcomings in the prior art and to provide a preservation tube for a sampling swab, which does not require oscillating elution, and facilitates subsequent detection and sampling.

In order to overcome the above technical problems, the technical solutions adopted in the present invention are as follows.

It is provided a preservation tube for a sampling swab, which includes a tube body, a first cavity for storing a sample releasing agent and a second cavity for placing sampling swab are provided in the tube body, the first cavity is in communication with the second cavity, and a central axis of the second cavity deviates from a central axis of the tube body.

For the preservation tube for the sampling swab according to the present invention, the sampling swab is placed in the second cavity, and moves up and down and rotates to elute in the second cavity, nucleic acid sample of the sampling swab are evenly distributed in the sample releasing agent, and can be used for detection after sucking the sample releasing agent in the first cavity. the present invention eliminates the process of oscillating elution to extract the nucleic acid sample, and the swab is placed vertically in the second cavity arranged to deviate from a center of the tube body, providing operation space for the sampling operation, simplifying the nucleic acid detection operation process, facilitating clinical trial operation, and reducing the risk of infection during the detection process.

Further, the central axis of the first cavity coincides with the central axis of the tube body, and a side portion of the second cavity is attached to an inner wall of the tube body. The first cavity is used to store the sample releasing agent, and its location is limited to facilitate subsequent automatic detection and sampling; and the location of the second cavity is limited so that the sampling swab is attached to the inner wall of the tube body, so that the sampling swab can stand stably in the second cavity, preventing the sampling swab from tilting to adversely affect the detection and sampling.

Further, a top portion of the tube body is provided with a first connection portion for connecting a tube cap, and a bottom portion of the tube body is provided with a fixing portion. The first connection portion is used for connecting the tube cap to the tube body, and keeping the sampling swab and the sample releasing agent under seal in the preservation tube; and the fixing portion is used for the matching between the tube body and a fixing table or a fixing instrument, which facilitates the automation of rotation operation of the tube cap.

Further, a top portion of the first cavity and the second cavity are connected with a second connection portion, the second connection portion surrounds between an outer edge of the top portion of the first cavity and the second cavity and the inner wall of the tube body. After the tube body is connected to the tube cap, a confined space is formed among the second connection portion, the first cavity, the second cavity, the tube body and the tube cap, and the swab and the sample releasing agent are stored in the confined space, which can effectively ensure the stability of sample storage.

Further, an inner wall of the second cavity is provided with a plurality of first protrusions. On the one hand, the nucleic acid sample can be better eluted when moving up and down and rotating the sampling swab, on the one hand, it facilitates the sampling swab to stand stably in the second cavity and not easy to fall.

Further, the first protrusion is a first rib, and the first rib is one of or a combination of more of a vertical rib, a horizontal rib, a bevel rib and a spiral rib. The shape of the first rib doesn't serve as a restrictive provision of the present invention, and other friction structures that can increase the friction between the sampling swab and the inner wall of the second cavity to improve the elution effect of the sampling swab can be suitable for the present invention.

Further, the first protrusion is a first emboss. The first emboss can be connected to form one of or a combination of more of a vertical rib structure, a horizontal rib structure, a bevel rib structure and a spiral rib structure, and can also be processed to form an irregular rib structure as needed, which not only has a better elution effect when moving up and down or rotating the sampling swab, but also saves the amount of preparation raw materials.

Further, both an inner side and a bottom portion of the second cavity are evenly distributed with a plurality of second protrusions. The first protrusion at the side portion can have an elution effect to the nucleic acid sample at the side portion of the sampling swab, and the second protrusion at the bottom portion can have an elution effect to the nucleic acid sample at the bottom portion of the sampling swab, which can improve the elution effect of the sample on the sampling swab when the sampling swab moves up and down and rotates.

Further, the second protrusion is a second rib, one end of the second rib is located in a center of the bottom portion of the second cavity, and the other end of the second rib is connected to the first protrusion. The position and shape arrangement of the second rib are preference for simplifying the mold structure, simplifying the molding process, designing beautifully, and improving the elution effect, but not as a restrictive provision of the present invention.

Further, the second protrusion is a second emboss. The first emboss can be connected to form a radial rib structure distributed along a radial direction of the bottom portion of the second cavity, which not only has a better elution effect when the sampling swab rotates, but also saves the amount of preparation raw materials.

Further, the first cavity is a taper hole, the second cavity is a cylindrical hole, and a depth of the second cavity is greater than a depth of the first cavity. An outer edge of one end of the first cavity and an outer edge of one end of the second cavity are both connected to the second connecting part, and the other end of the second cavity is arranged lower than the other end of the first cavity to increase the stability of the erect storage of the sampling swab.

Further, the first cavity is a taper hole, the second cavity is a cylindrical hole, the first cavity and the second cavity are partially overlapped to form a first side rib and a second side rib, a distance between the first side rib and the second side rib is not greater than the smallest diameter of the sampling swab, and the sampling swab cannot pass through a gap between the first side rib and the second side rib. The arrangement of the gap between the first side rib and the second side rib is a preference made to obtain good processing performance and sampling swab stabilization, and is not as a provision of the present invention.

Compared with the prior art, the beneficial effects of the present invention are as follows:

a preservation tube for a sampling swab according to the present invention, omits the process of oscillating elution to extract the nucleic acid sample, and the swab is placed vertically in the second cavity arranged to deviate from a center of the tube body, providing operation space for the sampling operation, simplifying the nucleic acid detection operation process, and facilitating clinical trial operation, reducing the risk of infection during the detection process.

DETAILED DESCRIPTION

The present invention will be further described below in combination with specific implementations. In particular, the accompanying drawings are only used for exemplary explanation, and they are only schematic diagrams, rather than physical drawings, and cannot be understood as a limitation of this patent application. In order to better illustrate the embodiments of the present invention, some parts in the accompanying drawings may be omitted, enlarged or shrunk, and do not represent the size of the actual product. For those skilled in the art, it is understandable that some well-known structures in the accompanying drawings and the explanations thereof may be omitted.

The same or similar reference numbers in the accompanying drawings of the embodiments of the present invention correspond to the same or similar parts. In the illustration of the present invention, it should be understood that if the terms "upper", "lower", "left", "right", etc. indicating the orientation or positional relationship are based on the orientation or positional relationship shown in the accompanying drawings, which is only for the convenience of describing the present invention and simplifying the illustration, rather than indicating or implying that the referred device or element must have a specific orientation, or be constructed and operated in a specific orientation. Therefore, the terms describing the positional relationship in the accompanying drawings are only used for exemplary explanation, and cannot be understood as a limitation of the patent application. For those of ordinary skill in the art, the specific meaning of the above terms can be understood according to specific circumstances.

Embodiment 1

The first embodiment of a preservation tube for a sampling swab of the present invention is shown in FIG. 1 to FIG. 4, including a tube body 1, a first cavity 11 for storing a sample releasing agent and a second cavity 12 for placing the sampling swab are provided in the tube body 1, the first cavity 11 is in communication with the second cavity 12, and a central axis of the second cavity 12 deviates from a central axis of the tube body 1. In the present embodiment, the elution process of the sampling swab moving up and down and rotating in the second cavity 12 can be made as a mark attached to an outer wall of the tube body 1.

When implementing the present embodiment, the sampling swab is placed in the second cavity 12 after sampling, and moves up and down and rotates in the second cavity 12 to elute, the nucleic acid sample on the sampling swab are evenly distributed in the sample releasing agent, and can be used for detection after sucking the sample releasing agent in the first cavity 11, so as to eliminate the process of oscillating elution to extract the nucleic acid sample, and the swab is placed vertically in the second cavity 12 arranged to deviate from a center of the tube body 1, providing operation space for the sampling operation, simplifying the nucleic acid detection operation process, and facilitating clinical trial operation, reducing the risk of infection during the detection process.

In order to make the sampling swab stand stably in the second cavity 12, in this embodiment, a size of the second cavity 12 can be arranged so that an inner wall of the second cavity 12 gently squeezes a head portion of the sampling swab. Specifically, the size of the second cavity 12 is between the maximum diameter of the head portion of the sampling swab and the diameter of a stem portion of the sampling swab. However, it should be noted that the arrangement of the size of the second cavity 12 is a preference for better stabilizing the sampling swab, and is not a restrictive provision of the present invention.

In this embodiment, the communication form between the first cavity 11 and the second cavity 12 can be multiple communication forms as follows: the first cavity 11 is in communication with a side portion of the second cavity 12, when the side portion is in communication, a sufficient amount of the sample releasing agent should be added into the first cavity 11 and the second cavity 12, so that a liquid level of the sample releasing agent is higher than a lowest point of communication between the first cavity 11 and the second cavity 12 to ensure that the sample releasing agent can flow freely between the first cavity 11 and the second cavity 12; the first cavity 11 is in communication with a bottom portion of the second cavity 12, when the bottom portion is in communication, a bottom portion of the first cavity 11 can be arranged under the bottom portion of the second cavity 12, so that the sample releasing agent containing the nucleic acid sample can flow smoothly into the first cavity 11 for subsequent detection and sampling. Of course, the communication form between the first cavity 11 and the second cavity 12 is not limited to the above two forms, and other communication forms that can ensure that the sample releasing agent flows in the first cavity 11 and the second cavity 12 and the sample release agent from which the nucleic acid sample is eluted flows to the first cavity 11 for storage are suitable for the present invention.

In order to further limit the storage position of the sampling swab in the preservation tube and avoid the improper position of the sampling swab from affecting the detection and sampling operation, this embodiment further limits the distribution positions of the first cavity 11 and the second cavity 12 in the tube body 1. Specifically, in this embodiment, the central axis of the first cavity 11 coincides with the central axis of the tube body 1, and the side portion of the second cavity 12 is attached to an inner wall of the tube body 1. In this way, the sampling instrument can be easily inserted into the first cavity 11 to suck the sample releasing agent, and the sampling swab is close to the inner wall of the tube body 1 at a side in the second cavity 12, so that the sampling swab can be erectly stored stably.

Figure 3:
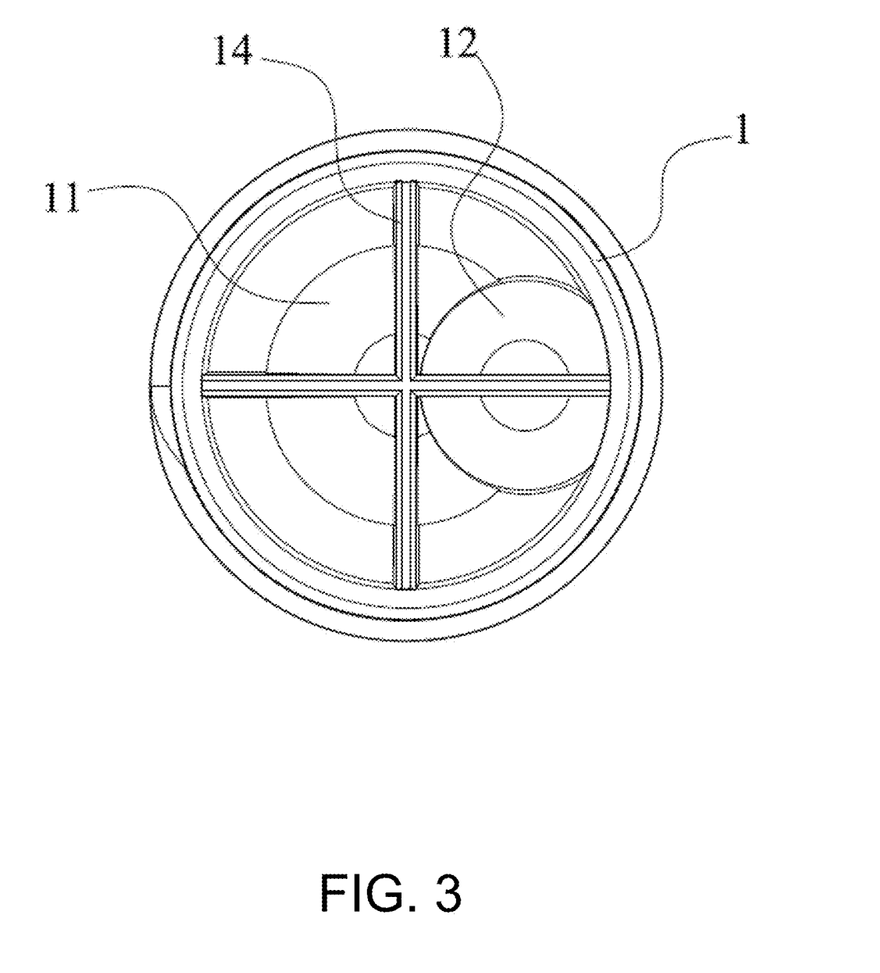
FIG. 3 is a bottom view of the preservation tube for the sampling swab according to Embodiment 1.

During the transportation of the preservation tube, the preservation tube should be sealed. Therefore, in this embodiment, a top portion of the tube body 1 is provided with a first connection portion 13 for connecting the tube cap 2. In order to be suitable for the automatic operation of the instrument in the detection process, in the present embodiment, a bottom portion of the tube body 1 is provided with a fixing portion 14, a structure of the fixing portion 14 can be arranged according to the structure of a fixing instrument or a fixing table, and in the present embodiment, one end of the fixing portion 14 is flush with the bottom portion of the tube body 1, and the other end of the fixing portion 14 can extend upward to an edge of a top portion of the first cavity 11 and the second cavity 12. One side portion of the second cavity 12 is tangent to the fixing portion 14 and the other side is attached to the inner wall of the tube body 1. In this embodiment, the connecting part is an external thread provided on an outer wall of the tube body 1, and the tube body 1 and the tube cap 2 are connected by a thread, the connection is stable, and can facilitate automatic operation. As shown in FIG. 3, the fixing portion 14 is arranged as a cross structure, during operation of the tube cap 2, the cross structure matches and fixed with the fixing table to prevent the tube body 1 from rotating with the tube cap 2 when the tube cap 2 is rotated. However, it should be noted that the cross structure is preference for both better fixing effect and better processing and forming performance, and is not a limitation provision of the present invention. The structure of the fixing portion 14 in this embodiment can be designed and adapted according to the fixing table or the fixing instrument.

Figure 1:
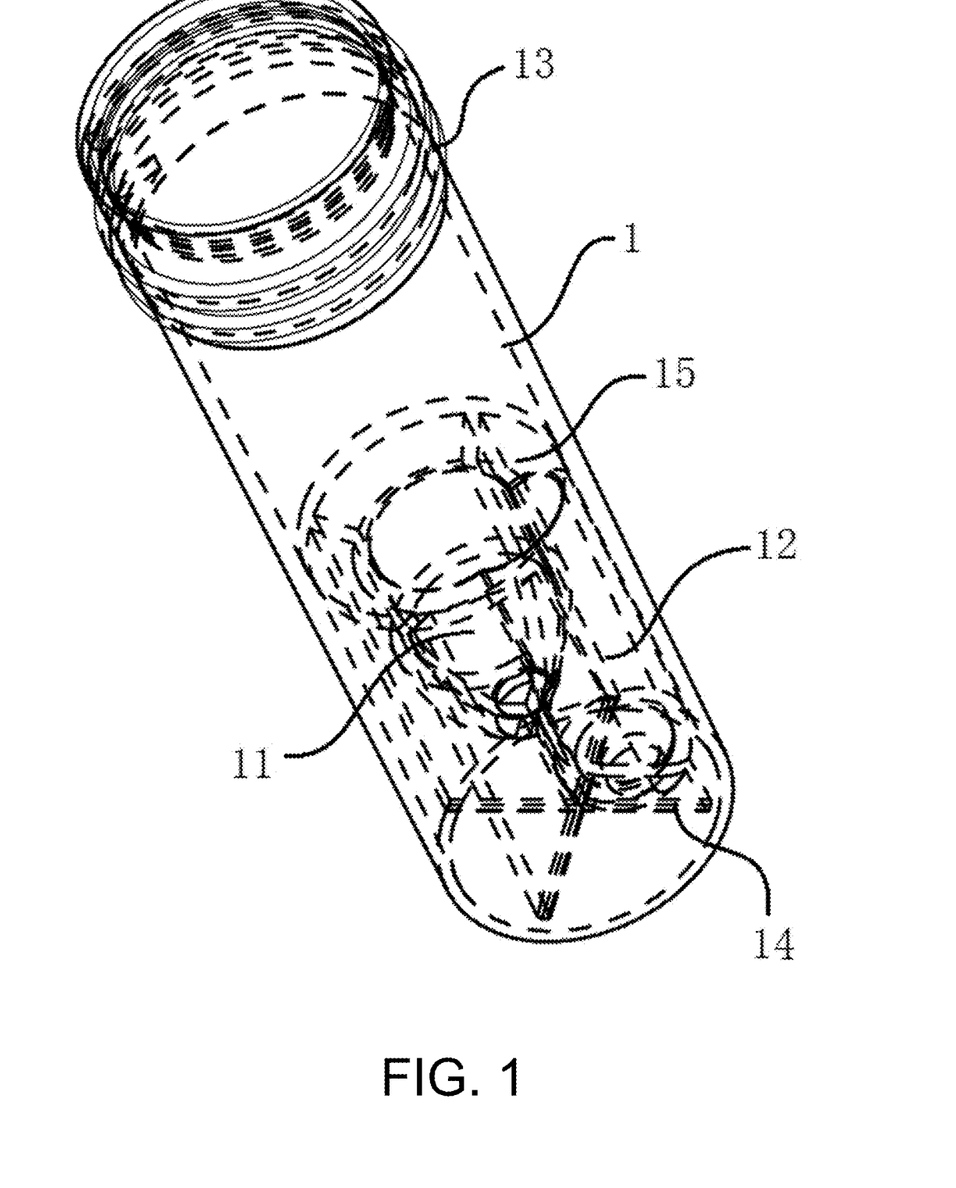
FIG. 1 is a perspective view of a preservation tube for a sampling swab according to Embodiment 1.
Figure 2:
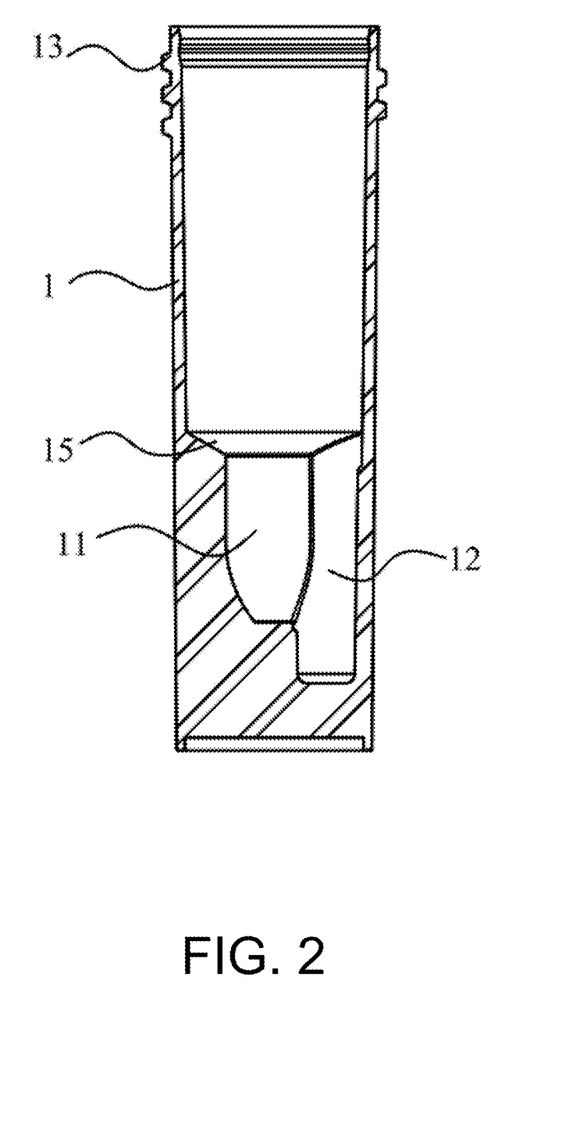
FIG. 2 is a schematic structural diagram of the preservation tube for the sampling swab according to Embodiment 1.
Figure 4:
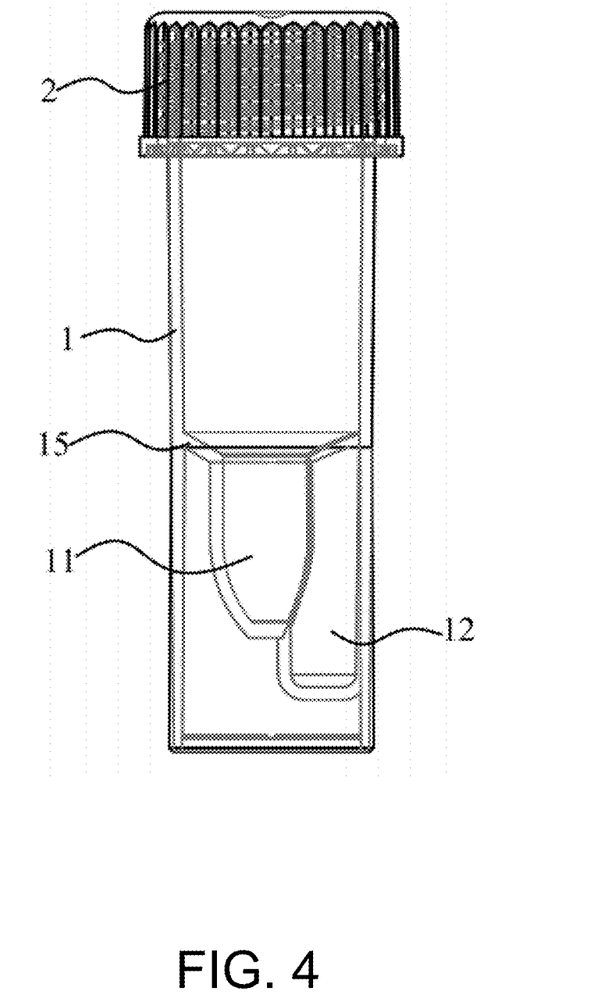
FIG. 4 is a schematic structural diagram of the preservation tube for the sampling swab installed with a tube cap according to Embodiment 1.

In order to reasonably distribute the positions of the first cavity 11 and the second cavity 12 in the tube body 1, in this embodiment, a second connection portion 15 is connected to the top portion of the first cavity 11 and the second cavity 12. The second connection portion 15 can be in a circular table shape and surrounds between an outer edge of the first cavity 11 and the second cavity 12 and the inner wall of the tube body 1, as shown in FIG. 2. After the tube body 1 is connected to the tube cap 2, a confined space is formed among the second connection portion 15, the first cavity 11, the second cavity 12, the tube body 1 and the tube cap 2, as shown in FIG. 4. The swab and the sample releasing agent are stored in the confined space, which can effectively ensure the stability of sample storage. Moreover, the second connection portion 15, the first cavity 11 and the second cavity 12 of this embodiment may be an integrally formed structure. The first cavity 11 and the second cavity 12 are partially overlapped. Cross sections of the first cavity 11 and the second cavity 12 have a gourd structure. A distance between the first side rib and the second side rib which are formed by the connection of the first cavity 11 and the second cavity 12 can be arranged according to the molding requirements and the shape and size of the sampling swab.

In order to give the preservation tube product better performance, wall thickness of the tube body 1, wall thickness of the first cavity 11, wall thickness of the second cavity 12, thickness of the fixing portion 14 and thickness of the second connection portion 15 of the preservation tube of this embodiment are equal to ensure the cooling effect during the molding process. Of course, this is only a preference made to obtain a preservation tube with better performance by using existing production equipment, and is not a restrictive provision of the present invention.

Embodiment 2

Figure 5:
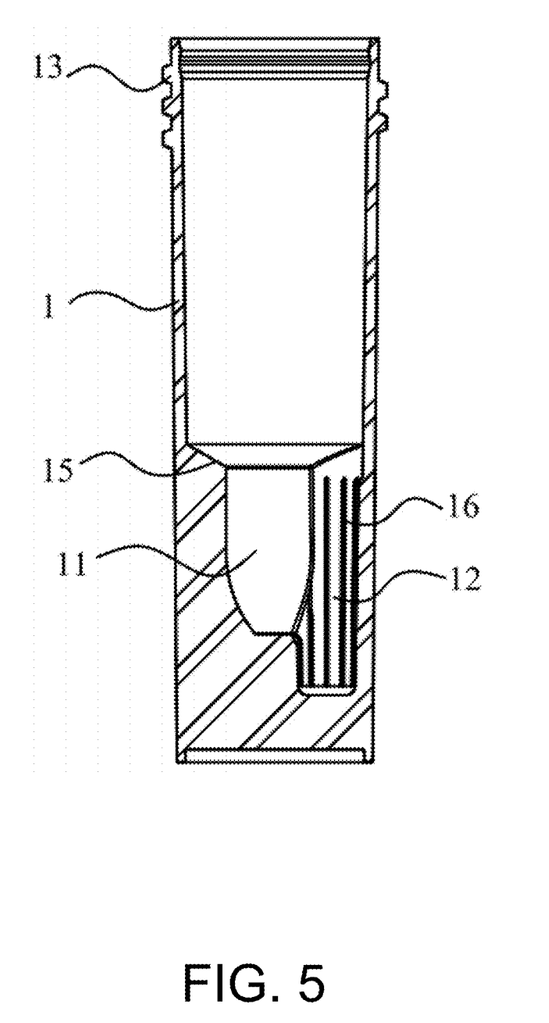
FIG. 5 is a schematic structural diagram of a preservation tube for a sampling swab according to Embodiment 2.
Figure 6:
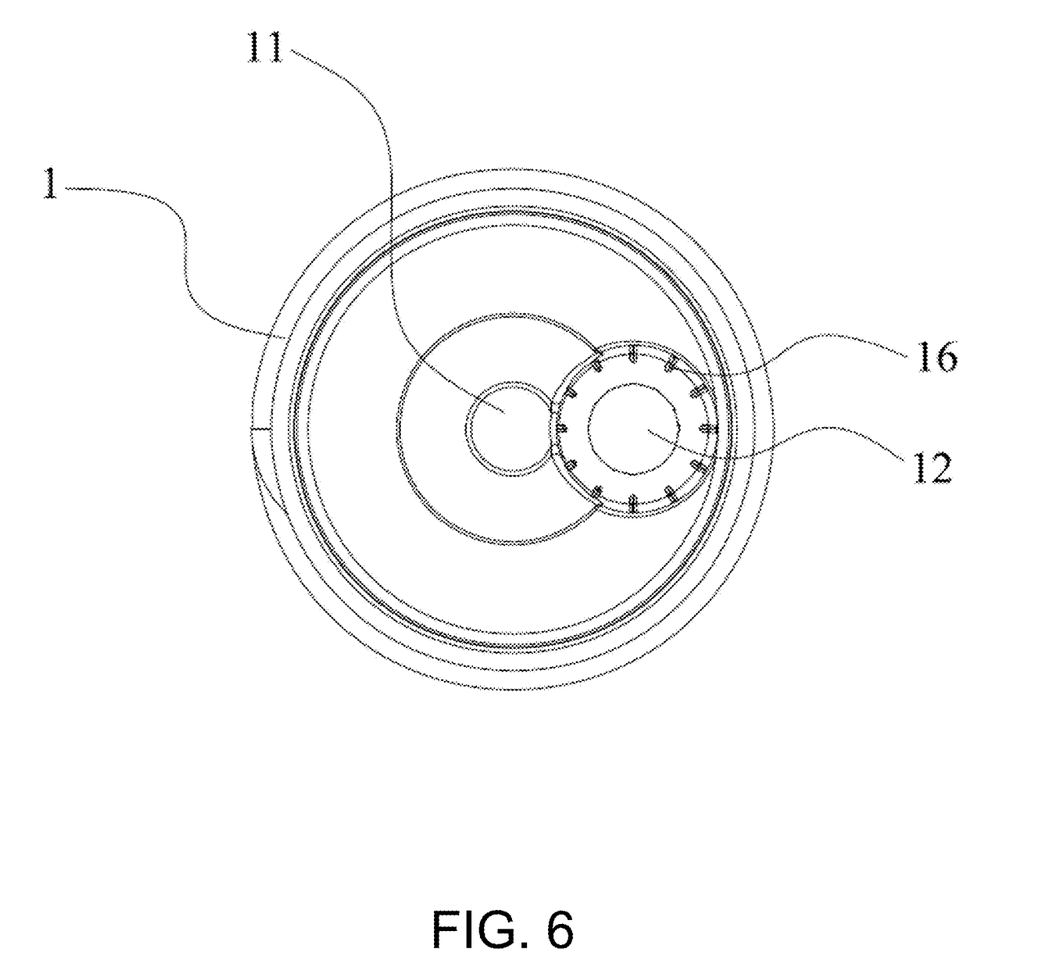
FIG. 6 is a top view of the preservation tube for the sampling swab according to Embodiment 2.

The second embodiment of the preservation tube for the sampling swab of the present invention is as shown in FIG. 5 to FIG. 6. This embodiment is the same as Embodiment 1, but the difference is that in this embodiment, the inner wall of the second cavity 12 is provided with a plurality of first protrusions 16. On the one hand, it can better elute the nucleic acid sample when moving up and down and rotating the sampling swab, and on the other hand, it facilitates the sampling swab to stand stably in the second cavity 12 and not easy to fall.

Specifically, the first protrusion 16 in the present embodiment is a first rib. The first rib is one of or a combination of more of a vertical rib, a horizontal rib, a bevel rib and a spiral rib. Of course, it should be noted that the shape of the first rib listed above is not served as a restrictive provision of the present invention, and other friction structures that can increase the friction between the sampling swab and the inner wall of the second cavity 12 to improve the elution effect of the sampling swab are suitable for the present invention.

The first rib of the present embodiment may preferably be a vertical rib, but the first rib arranging as the vertical rib is for to facilitating demolding of the tube body 1, and is not served as a restrictive provision of the present invention.

Moreover, the number of the first ribs in this embodiment can be set to 8 to 12, evenly surrounding the inner wall of the second cavity 12. However, it should be noted that the number of the first ribs is not served as a restrictive provision of the present invention. In this embodiment, the number of the first ribs can be increased or decreased according to the thickness of the first rib, the elution effect of the first rib, and structural parameters of the sampling swab.

Embodiment 3

This embodiment is the third embodiment of the preservation tube for the sampling swab. This embodiment is the same as Embodiment 2, but the difference is that in this embodiment, the inner wall of the second cavity 12 is provided with a plurality of first emboss, rather than a continuous structure like the first rib in the second embodiment. Compared with Embodiment 2, this embodiment can obtain a better elution effect and can save the amount of preparation raw materials for the tube body 1.

The first emboss in the present embodiment can be connected to form one of or a combination of more of a vertical rib structure, a horizontal rib structure, a bevel rib structure and a spiral rib structure, and can also be processed to form an irregular rib structure as needed. Moreover, the shape of the first emboss of this embodiment can be arranged to a hemispherical, rectangular, or other friction structure which can increase the friction between the sampling swab and the second cavity 12 when the sampling swab moves up and down or rotates.

In order to facilitate the processing of the first protrusion 16 and the demolding of the first protrusion 16, a plurality of the first embosses of this embodiment can form a vertical rib structure and evenly surround the inner wall of the second cavity 12.

Embodiment 4

Figure 7:
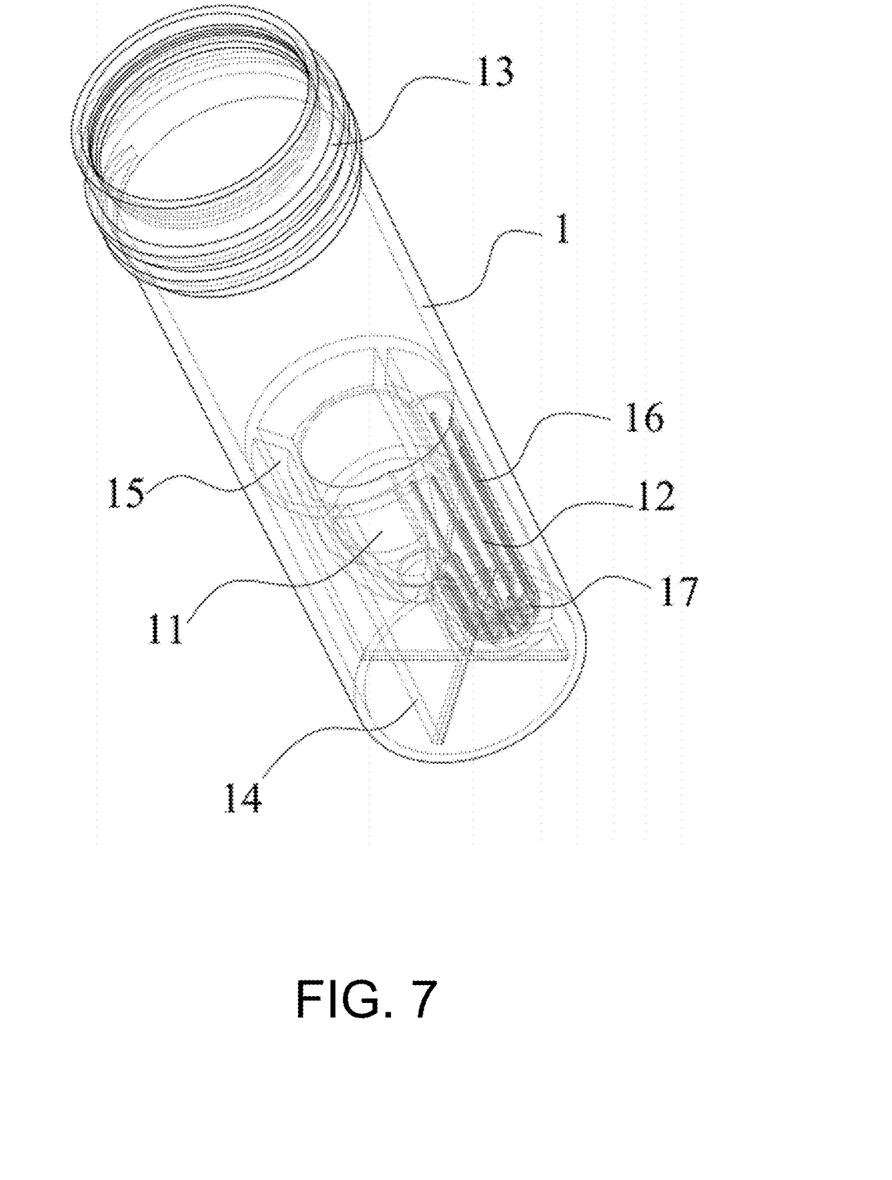
FIG. 7 is a perspective view of a preservation tube for a sampling swab according to Embodiment 4.
Figure 8:
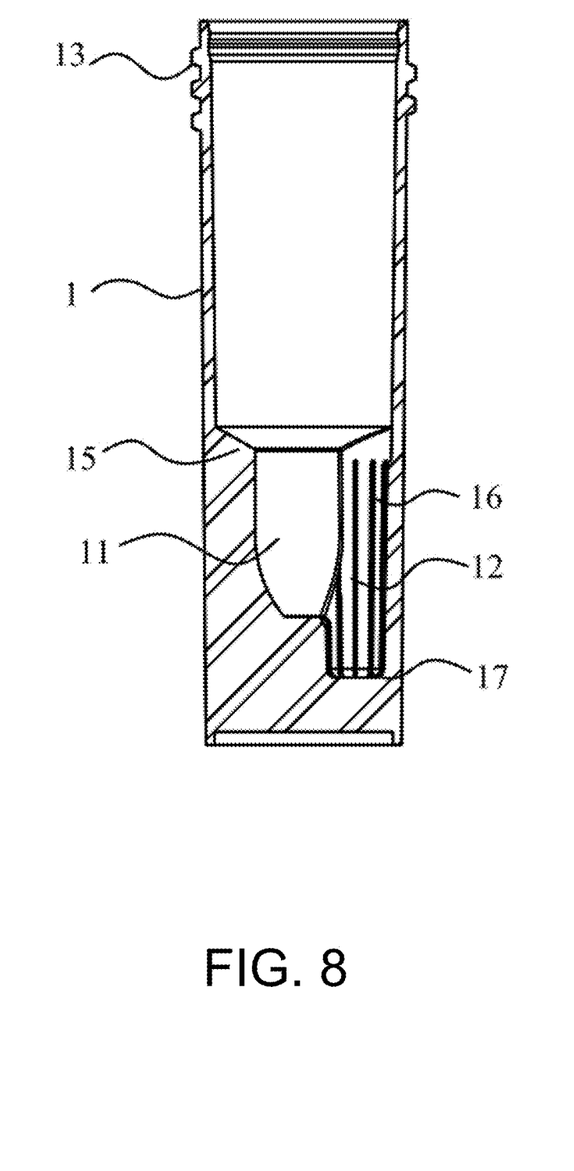
FIG. 8 is a schematic structural diagram of the preservation tube for the sampling swab according to Embodiment 4.
Figure 9:
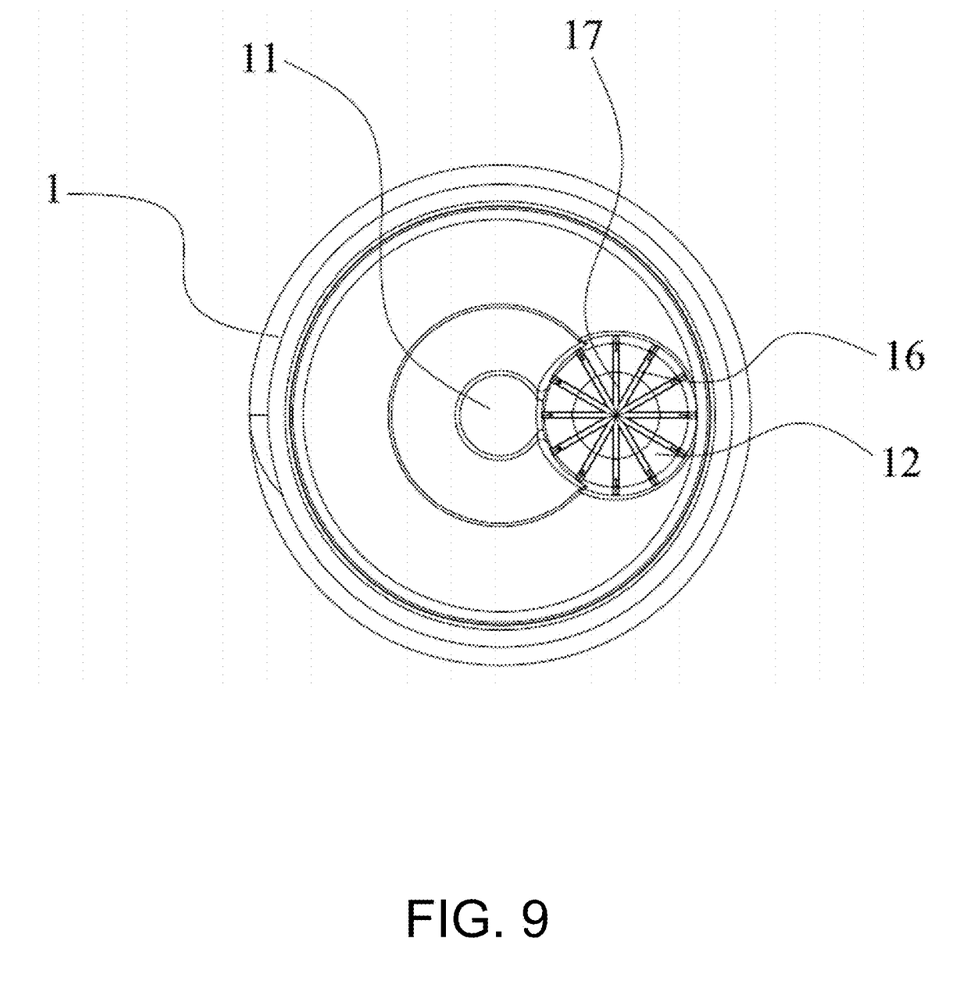
FIG. 9 is a top view of the preservation tube for the sampling swab according to Embodiment 4.

The fourth embodiment of the preservation tube for the sampling swab of the present invention is as shown in FIG. 7 to FIG. 9. This embodiment is the same as Embodiment 2 or Embodiment 3, but the difference is that: when the sampling swab is used for sampling, the nucleic acid sample not only adheres to the side portion of the sampling swab, but also adheres to the bottom portion of the sampling swab, so in this embodiment, in addition that the first protrusions 16 are provided to surround the sidewall of the second cavity 12, the second protrusions 17 are also provided on the inner side and the bottom portion of the second cavity 12, such that both the nucleic acid sample at the side portion of the sampling swab and the nucleic acid sample at the bottom portion of the sampling swab can be eluted. Specifically, the second protrusion 17 of this embodiment is a second rib, one end of the second rib is arranged at a center of the bottom portion of the second cavity 12, and the other end of the second rib is connected to the first protrusion 16. When the first protrusion 16 is the first rib and the vertical rib, the number of second ribs is equal to the number of the first ribs, and the first ribs and second ribs can be connected to form an integrated rid structure, and the mold structure is simple in design, easy to mold, beautiful in design, and has a good elution effect. However, it should be noted that the structure and number design of the second rib in this embodiment is a preference made for beautiful design and convenient processing, and is not served as a restrictive provision of the present invention, and other edge structures and edge numbers that can achieve the elution effect are also suitable for the present invention.

Embodiment 5

This embodiment is the same as Embodiment 2 or Embodiment 3, but the difference is that, in this embodiment, in addition that the first protrusions 16 are provided to surround the sidewall of the second cavity 12, the second protrusions 17 are also provided on the inner side and the bottom portion of the second cavity 12. The second protrusion 17 in this embodiment is a second emboss, rather than a continuous structure similar to the second rib in Embodiment 4. Compared with Embodiment 4, this embodiment can obtain a better elution effect and can save the amount of preparation raw materials for the tube body 1.

The second embosses in this embodiment can be connected to form a regular arrangement structure, or can be processed as needed to form an irregular rib structure. Moreover, the shape of the second emboss of this embodiment can be arranged to a hemispherical, rectangular, or other friction structure that can increase the friction between the sampling swab and the second cavity 12 when the sampling swab moves up and down or rotates.

Embodiment 6

This embodiment is the same as any one of Embodiment 1 to Embodiment 5, but the difference is that, the first cavity 11 in this embodiment is a taper hole, the second cavity 12 is a cylindrical hole, and a depth of the second cavity 12 is greater than a depth of the first cavity 11, as shown in FIG. 4. Arranging the first cavity 11 as the taper hole facilitates collecting and increasing the liquid surface depth of the sample releasing agent in the first cavity 11, which facilitates subsequent detection and sampling. The depth of the second cavity 12 is greater than the depth of the first cavity 11, the bottom portion of the second cavity 12 is located below the bottom portion of the first cavity 11, and the sampling swab can be stably standing in the second cavity 12, preventing the impact of falling of the sampling swab on the detection and sampling operation.

Embodiment 7

Figure 10:
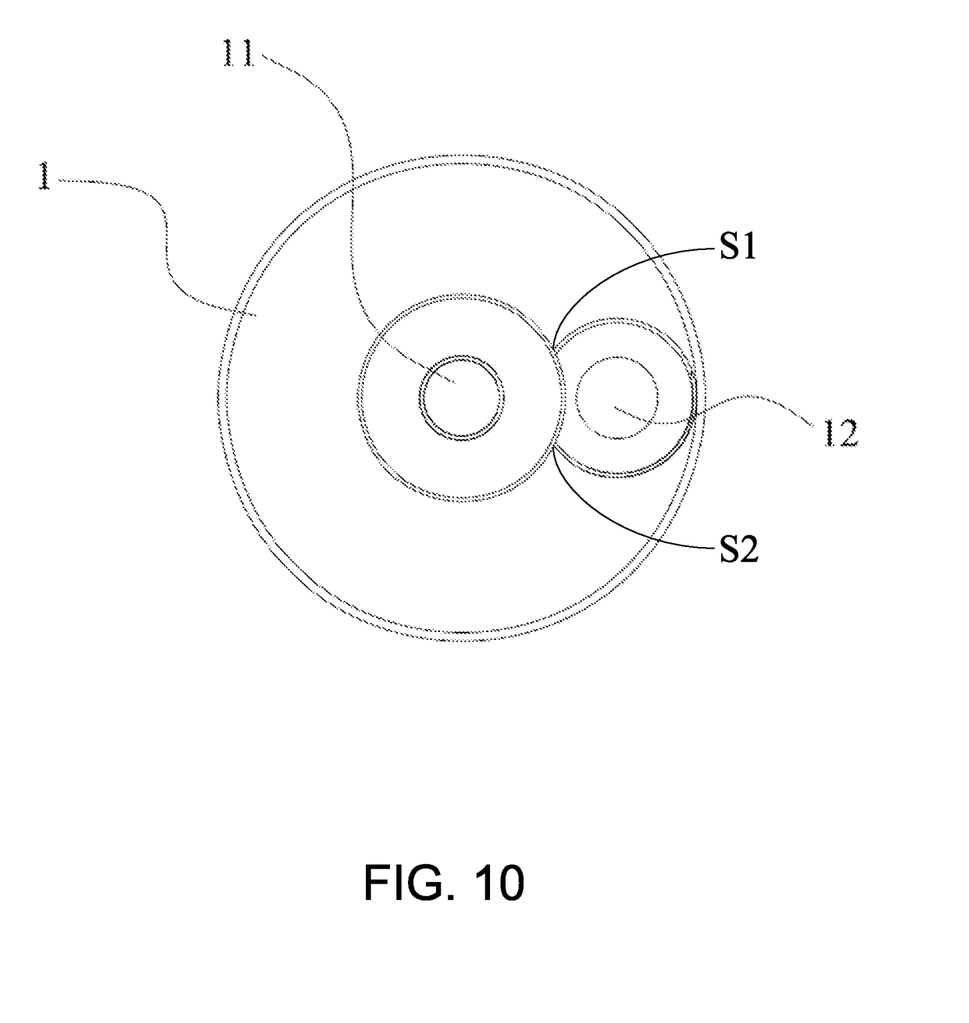
FIG. 10 is a top view of the preservation tube for the sampling swab according to Embodiment 7.

This embodiment is the same as any one of Embodiment 1 to Embodiment 5, but the difference is that, the first cavity 11 in this embodiment is a taper hole, the second cavity 12 is a cylindrical hole, a diameter of the first cavity 11, a diameter of the second cavity 12 and a diameter of the tube body 1 are collinear, the first cavity 11 and the second cavity 12 are partially overlapped to form a first side rib S1 and a second side rib S2, and a distance between the first side rib S1 and the second side rib S2 is not greater than the smallest diameter of the sampling swab, as shown in FIG. 10. When implemented, it does not affect the communication between the first cavity 11 and the second cavity 12, and the sample releasing agent can flow freely between the first cavity 11 and the second cavity 12, and it can effectively prevent the sampling swab in the second cavity 12 from tilting to a side of the first cavity 11. It should be noted that the arrangement of a gap between the first side rib S1 and the second side rib S2 is a preference to obtain good processing performance and stable sampling swab, and is not a provision of the present invention. The present invention can also connect a side plate between the first side rib S1 and the second side rib S2, and design a small opening or a slot on the side plate to realize the communication between the first cavity 11 and the second cavity 12 while preventing the sampling swab from tilting.

Obviously, the above embodiments of the present invention are merely examples to clearly illustrate the present invention, and are not a limitation on the implementation of the present invention. For those of ordinary skill in the art, on the basis of the above explanation, other variations or changes in different forms can also be made. It is not necessary and impossible to enumerate all the implementations herein. Any modifications, equivalent replacements and improvements made within the spirit and principle of the present invention shall be included in the scope of protection of the claims of the present invention.

What is claimed is:

1. A preservation tube for a sampling swab, comprising a tube body, wherein a first cavity for storing a sample releasing agent and a second cavity for placing the sampling swab are provided in the tube body, the first cavity is in communication with the second cavity, and a central axis of the second cavity deviates from a central axis of the tube body,
   wherein the first cavity is a taper hole, the second cavity is a cylindrical hole, the first cavity and the second cavity are partially overlapped to form a first side rib and a second side rib, and a distance between the first side rib and the second side rib is not greater than the smallest diameter of the sampling swab,
   a shape of a projection of the first cavity projected onto a bottom surface of the tube body is a first circle, a shape of a projection of the second cavity projected onto the bottom surface of the tube body is a second circle, the first circle only partially overlaps the second circle, a part of the first circle does not overlap the second circle, the first side rib and the second side rib are formed at positions where an edge of the first circle and an edge of the second circle overlap, wherein top portions of the first cavity and the second cavity are connected with a second connection portion, the second connection portion surrounds between an outer edge of the top portions of the first cavity and the second cavity and the inner wall of the tube body, the second connection portion is a cone with an opening expanding upwards.

2. The preservation tube for the sampling swab according to claim 1, wherein the central axis of the first cavity coincides with the central axis of the tube body, and a side portion of the second cavity is attached to an inner wall of the tube body.

3. The preservation tube for the sampling swab according to claim 1, wherein a top portion of the tube body is provided with a first connection portion for connecting a tube cap, and a bottom portion of the tube body is provided with a fixing portion.

4. The preservation tube for the sampling swab according to claim 1, wherein an inner wall of the second cavity is provided with a plurality of first protrusions.

5. The preservation tube for the sampling swab according to claim 4, wherein the first protrusion is a first rib or a first emboss, and the first rib is one of or a combination of at least two of a vertical rib, a horizontal rib, a bevel rib and a spiral rib.

6. The preservation tube for the sampling swab according to claim 4, wherein both an inner side and a bottom portion of the second cavity are evenly distributed with a plurality of second protrusions.

7. The preservation tube for the sampling swab according to claim 6, wherein the second protrusion is a second rib or a second emboss, one end of the second rib is located in a center of the bottom portion of the second cavity, and the other end of the second rib is connected to the first protrusion.

8. The preservation tube for the sampling swab according to claim 1, wherein a depth of the second cavity is greater than a depth of the first cavity.

9. The preservation tube for the sampling swab according to claim 2, wherein a depth of the second cavity is greater than a depth of the first cavity.

10. The preservation tube for the sampling swab according to claim 3, wherein a depth of the second cavity is greater than a depth of the first cavity.

11. The preservation tube for the sampling swab according to claim 4, wherein a depth of the second cavity is greater than a depth of the first cavity.

12. The preservation tube for the sampling swab according to claim 5, wherein a depth of the second cavity is greater than a depth of the first cavity.

* * * * *